(12) United States Patent
Ramakrishna et al.

(10) Patent No.: US 10,464,873 B2
(45) Date of Patent: Nov. 5, 2019

(54) PROCESS FOR PREPARATION OF 1-[2-(DIMETHYL AMINO)-1-(4-HYDROXYPHENYL) ETHYL]-CYCLOHEXANOL AND SALTS THEREOF

(71) Applicant: R L FINECHEM PRIVATE LIMITED, Bengaluru, Karnataka (IN)

(72) Inventors: Ramesha A. Ramakrishna, Bengaluru (IN); Siddegowda S. Maravanahalli, Bengaluru (IN)

(73) Assignee: R L FINECHEM PRIVATE LIMITED, Bengaluru (IN)

( * ) Notice: Subject to any disclaimer, the term of this patent is extended or adjusted under 35 U.S.C. 154(b) by 0 days.

(21) Appl. No.: 15/548,304

(22) PCT Filed: Mar. 31, 2017

(86) PCT No.: PCT/IB2017/051843
§ 371 (c)(1),
(2) Date: Aug. 2, 2017

(87) PCT Pub. No.: WO2018/146529
PCT Pub. Date: Aug. 16, 2018

(65) Prior Publication Data
US 2018/0251417 A1    Sep. 6, 2018

(30) Foreign Application Priority Data
Feb. 9, 2017  (IN) .............. 201741004702

(51) Int. Cl.
| C07C 37/50 | (2006.01) |
| C07C 39/06 | (2006.01) |
| C07C 215/00 | (2006.01) |
| C07C 213/00 | (2006.01) |
| C07C 55/10 | (2006.01) |

(52) U.S. Cl.
CPC .............. *C07C 37/50* (2013.01); *C07C 39/06* (2013.01); *C07C 55/10* (2013.01); *C07C 213/00* (2013.01); *C07C 215/00* (2013.01)

(58) Field of Classification Search
None
See application file for complete search history.

(56) References Cited

U.S. PATENT DOCUMENTS

| 4,535,186 A | 8/1985 | Husbands et al. |
| 6,689,912 B2 | 2/2004 | Weber |
| 7,491,848 B2 | 2/2009 | Pospisilik et al. |
| 2005/0197392 A1 | 9/2005 | Jerussi et al. |
| 2011/0263718 A1* | 10/2011 | Gore ................. C07C 213/08 514/654 |

FOREIGN PATENT DOCUMENTS

| WO | WO 02/064543 | * | 8/2002 |
| WO | 2007/120923 A1 | | 10/2007 |
| WO | 2009/053731 A1 | | 4/2009 |
| WO | 2009/084037 A2 | | 7/2009 |
| WO | 2010/013050 A1 | | 2/2010 |
| WO | 2010/079046 A1 | | 7/2010 |

OTHER PUBLICATIONS

Jun. 22, 2017 Search Report issued in International Patent Application No. PCT/IB2017/051843.
Ranu et al., "Dealkylation of Ethers. A Review" Organic Preparations and Procedures International: The New Journal for Organic Synthesis, 1996, vol. 28, Issue 4, pp. 371-409.
Marcello Tiecco, "Selective Dealkylations of Aryl Alkyl Ethers, Thioethers, and Selenoethers," Synthesis 1988, Issue 10, pp. 749-759.
1089/KOL/2007 A; Lupin Limited; Apr. 10, 2009.
Jun. 22, 2017 Written Opinion issued in International Patent Application No. PCT/IB2017/051843.

* cited by examiner

*Primary Examiner* — Ana Z Muresan
(74) *Attorney, Agent, or Firm* — Oliff PLC

(57) ABSTRACT

A high yield process of preparation of [1-[2-(Dimethyl-amino)-1-(4-hydroxyphenyl)ethy]-cyclohexanol] through potassium salt mediated demethylation of [1-[2-(Dimethyl amino-1-(4-methoxyphenyl) ethyl cyclohexanol] in monoethylene glycol under phase transfer conditions, as well as the preparation of salt of [1-[2-(Dimethylamino)-1-(4-hydroxyphenyl)ethyl]-cyclohexanol].

16 Claims, 1 Drawing Sheet

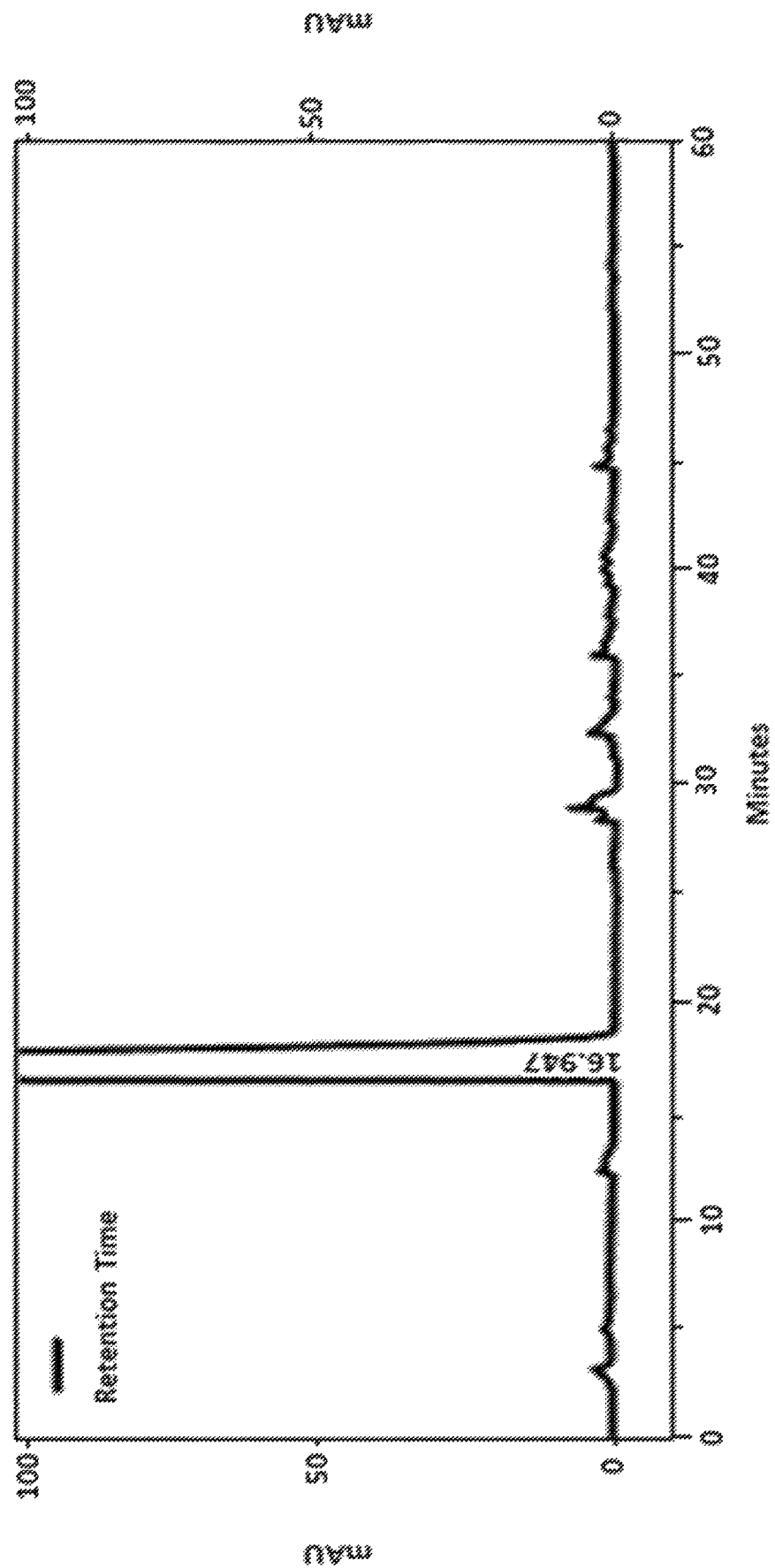

PROCESS FOR PREPARATION OF 1-[2-(DIMETHYL AMINO)-1-(4-HYDROXYPHENYL) ETHYL]-CYCLOHEXANOL AND SALTS THEREOF

FIELD OF INVENTION

The present invention relates to the field of antidepressants. More specifically to phenyl ethylamine derivatives for the treatment of central nervous system (CNS) related disorders. In particular the invention relates to the preparation of Desvenlafaxine and its salts, a selective serotonin and norepinephrine reuptake inhibitor for the treatment of CNS related disorders.

BACKGROUND OF INVENTION

Chemical imbalances in the human body are responsible for changes in mood and behaviour of a person. Antidepressants are a class of drugs that reduce symptoms of depressive disorders by correcting chemical imbalances of neurotransmitters in the brain. They are usually used to treat several conditions for example depression, generalized anxiety disorder, agitation, obsessive compulsive disorders and the like. Most often prescribed antidepressant drugs include Venlafaxine which are commercially available under the tradename Effexor, Lanvexin, Viepax and Trevilor. 1-[2-(Dimethylamino)-1-(4-methyloxyphenyl) ethyl] cyclohexanol, commonly known as Venlafaxine is an antidepressant of the serotonin-norepinephrine reuptake inhibitor (SNRI) class. Venlafaxine acts by inhibiting re-uptake of norepinephrine and serotonin, and is an alternative to the tricyclic antidepressants and selective re-uptake inhibitors. Venlafaxine is of the structural formula (I)

Formula (1)

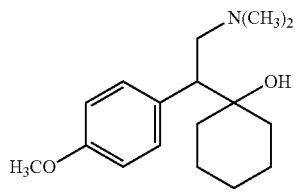

1-[2-(Dimethyl amino-1-(4-methoxyphenyl) ethyl cyclohexanol]

However due to profound side-effects observed, in the recent past Venlafaxine is not recommended as a first line of treatment. Also, Venlafaxine is extensively metabolized producing several metabolites.

However it is found that, [1-[2-(Dimethylamino)-1-(4-hydroxphenyl)ethyl]-cyclohexanol], commonly known as Desvenlafaxine is also an effective serotonin-norepinephrine reuptake inhibitor (SNRI) antidepressant and a safe treatment for major depressive disorders (TDD). Desvenlafaxine differs from Venlafaxine in that it is deficient of a methyl group attached to the phenolic ring. The structural formula of Desvenlafaxine (formula II) is as follows:

Formula II

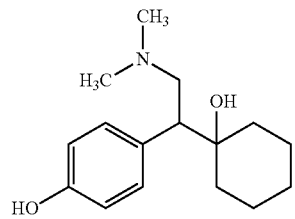

1-[2-(Dimethylamino)-1-(4-hydroxyphenyl)ethyl]-cyclohexanol]

Also, Desvenlafaxine is less extensively metabolized, when compared to Venlafaxine, with absolute bioavailability. Desvenlafaxine is administered as its salt Desvenlafaxinesuccinate and also an active metabolite of Venlafaxine.

Patent literature discloses the synthesis of Desvenlafaxine by the process of demethylation, of Venlafaxine using thiols, metal sulphides, lithium diphenylphosphide, alkyl aluminium hydride and the like. However these methods involve heavy metal catalyst, large volumes of solvents, and expensive reagents and very smelling sulphur reagents. Because of the odor during the manufacturing, special precautions and scrubbing is required for large scale manufacturing.

U.S. Pat. No. 4,535,186 discloses synthesis of Desvenlafaxine and its pharmaceutically acceptable salts specifically fumarate salt. The invention discloses a process for the preparation of desmethylvenlafaxine that involves use of a benzyl blocking group on the 4-hydroxy group of the phenyl ring.

U.S. Pat. No. 7,491,848 discloses synthesis of Desvenlafaxine, formed from Venlafaxine by the use of a demethylating agent comprising a metal sulfide, such as sodium sulfide, U.S. Pat. No. 6,689,912 discloses a method of preparing Desmethylvenlafaxine which comprises reacting Venlafaxine with a high molecular weight alkane or arene thiolate anion in an alcohol, ethylene glycol, ether of ethylene glycol, or mixture thereof, to provide desmethylvenlafaxine.

US20050197392 discloses a method for the preparation of desmethylvenlafaxine which involves demethylation of Venlafaxine using Lithium diphenylphosphide. The method involves extraction steps involving large volumes of solvent.

WO2010079046 discloses a process for the preparation of Desvenlafaxine and its salts, based on the demethylation of Venlafaxine by the use of alkyl aluminium or alkyl aluminium hydride compounds, particularly Di-isobutylaluminium hydride or tri-isobutylaluminium.

WO2007120923 provides a process for preparing Desvenlafaxine comprising-combining under reduced pressure venlafaxine, an organic solvent and a reagent consisting of: thiophenol, or sodium sulfide or Ci-Cs alkyl thiolate.

The aforementioned processes generally proceed with many side reactions thereby affecting the yield of Desvenlafaxine. They are complex and environmentally hazardous process. The reactions also emanate foul odour polluting the environment. The reagents used for the preparation are expensive and also the production of Desvenlafaxine on large scale is difficult and tedious.

Hence there is a need for an alternative economical, eco-friendly method of preparation of Desvenlafaxine. The process described in the present invention implements a simple, cost effective method of synthesis of Desvenlafaxine and also the salt of Desvenlafaxine by eliminating the use of expensive reagents.

BRIEF DESCRIPTION OF FIGURE

FIGURE: HPLC diagram indicating the purity level of the [1-[2-(Dimethylamino)-1-(4-hydroxyphenyl)ethyl]-cyclohexanol]

SUMMARY OF INVENTION

The invention relates to synthesis of Desvenlafaxine, [1-[2-(Dimethylamino)-1-(4-hydroxyphenyl)ethyl]-cyclohexanol] by the process of demethylation of 1-[2-(Dimethyl amino-1-(4-methoxyphenyl) ethyl cyclohexanol which is mediated through potassium salt in monoethylene glycol, under phase transfer conditions. The [1-[2-(Dimethyl-amino)-1-(4-hydroxyphenyl)ethyl]-cyclohexanol]synthesised by said process has a purity of more than 99% as measured by HPLC. The invention also relates to the preparation of [1-[2-(Dimethylamino)-1-(4-hydroxyphenyl)ethyl]-cyclohexanol]succinate with high yield. The process can be scaled up for mass production of [1-[2-(Dimethyl-amino)-1-(4-hydroxyphenyl)ethyl]-cyclohexanol] easily.

DETAILED DESCRIPTION OF INVENTION

The foregoing description of the embodiments of the invention has been presented for the purpose of illustration. It is not intended to be exhaustive or to limit the invention to the precise form disclosed as many modifications and variations are possible in light of this disclosure for a person skilled in the art in view of the Figures, description and claims. It may further be noted that as used herein and in the appended claims, the singular "a" "an" and "the" include plural reference unless the context clearly dictates otherwise. Unless defined otherwise, all technical and scientific terms used herein have the same meanings as commonly understood by person skilled in the art.

The present invention is in relation to a process for preparation of 1-[2-(Dimethylamino)-1-(4-hydroxyphenyl)ethyl]-cyclohexanol (formula (I)), comprising acts of

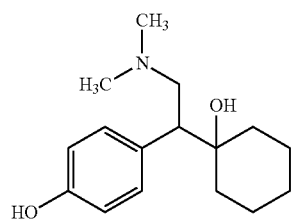

Formula I i) reacting 1-[2-(Dimethyl amino-1-(4-methoxyphenyl) ethyl cyclohexanol of formula (II)

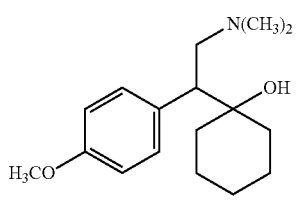

(Formula II)

with potassium salt, in an organic solvent to obtain a mixture;
ii) heating the mixture;
iii) diluting the mixture with water to obtain an aqueous phase; and
iv) acidifying the aqueous phase with an acidic reagent and filtering to obtain 1-[2-(Dimethylamino)-1-(4-hydroxyphenyl)ethyl]-cyclohexanol of formula (I).

In an embodiment of the present invention, the potassium salt is selected from a group comprising potassium hydroxide and potassium t-butoxide.

In an embodiment of the present invention, the organic solvent is selected from group comprising monoethylene glycol and other primary alcohols, preferably monoethylene glycol.

In another embodiment of the present invention, the mixture is heated to a temperature ranging from about 190° C. to about 220° C.

In still another embodiment of the present invention, acidifying the aqueous phase comprises adjusting the pH between 3 to 5 preferably 4, with a reagent selected from a group comprising an acidic reagent selected from a group comprising hydrochloric acid, phosphoric acid, acetic acid.

In yet another embodiment of the present invention, the process provides yield ranging from about 95% to about 99.5%.

In yet another embodiment of the present invention, the 1-[2-(Dimethylamino)-1-(4-hydroxyphenyl)ethyl]-cyclohexanol has a purity ranging from about 97.0% to about 99.5% measured by HPLC method.

The present invention is also in relation to a process for obtaining salt of 1-[2-(Dimethylamino)-1-(4-hydroxyphenypethyl]-cyclohexanol comprising acts of
a) reacting 1-[2-(Dimethyl amino-1-(4-methoxyphenyl) ethyl cyclohexanol of formula (II) with potassium salt in an organic solvent to obtain a mixture;

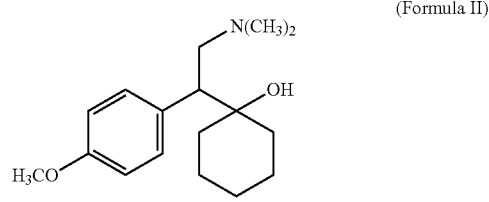

(Formula II)

b) heating the mixture;
c) diluting the mixture with water to obtain an aqueous phase;
d) acidifying the aqueous phase with an acidic reagent and filtering to obtain 1-[2-(Dimethylamino)-1-(4-hydroxyphenyl)ethyl]-cyclohexanol of formula (I).
e) reacting the 1-[2-(Dimethylamino)-1-(4-hydroxyphenyl)ethyl]-cyclohexanol of formula (I) with a reagent in an aqueous organic solvent to obtain salt.

In an embodiment of the present invention, the reagent is selected from a group comprising succinic acid, fumaric acid, oxalic acid; preferably succinic acid to obtain succinic acid salt of 1-[2-(Dimethyl amino-1-(4-methoxyphenyl) ethyl cyclohexanol.

In yet another embodiment of the present invention, salt of 1-[2-(Dimethylamino)-1-(4-hydroxyphenyl)ethyl]-cyclohexanol is of purity ranging from about 98.0 to about 99% measured by HPLC method.

The schematic diagram (I) shows the process of the synthesis of [1-[2-(Dimethylamino)-1-(4-hydroxyphenyl)ethyl]-cyclohexanol] and its succinate salt from 1-[2-(Dimethyl amino-1-(4-methoxyphenyl) ethyl cyclohexanol:

Scheme-I

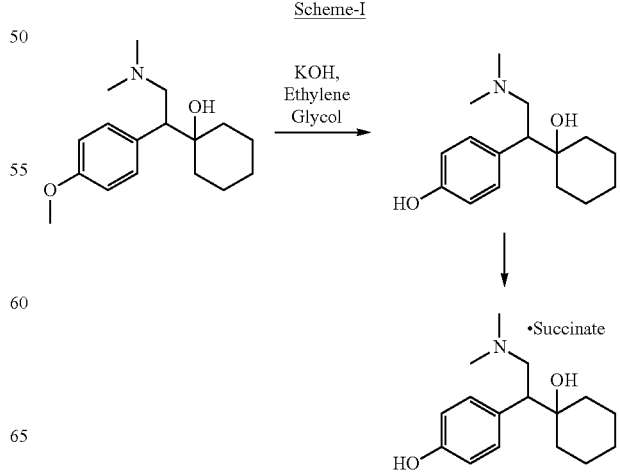

Demethylation of 1-[2-(Dimethyl amino-1-(4-methoxyphenyl) ethyl cyclohexanol to obtain [1-[2-(Dimethylamino)-1-(4-hydroxyphenyl)ethyl]-cyclohexanol] is performed under strong alkaline conditions in the presence of potassium hydroxide and an alcoholic solvent to obtain optimum yield of [1-[2-(Dimethylamino)-1-(4-hydroxyphenyl)ethyl]-cyclohexanol]. The target compound obtained by the high yield process described in the present invention has a purity of more than 99% as measured by HPLC. The process can be scaled up for mass production of [1-[2-(Dimethylamino)-1-(4-hydroxyphenyl)ethyl]-cyclohexanol], as commercially available eco friendly reagents are used in the reaction.

EXPERIMENTAL

The examples described below illustrates the process of synthesis of Desvenlafaxine, [1-[2-(Dimethylamino)-1-(4-hydroxyphenyl)ethyl]-cyclohexanol] however they do not limit the scope of the invention.

Example 1

To a clean flask, 250 g of 1-[2-(Dimethyl amino-1-(4-methoxyphenyl) ethyl cyclohexanol, 1 lt of ethylene glycol, 100 g of polyethylene glycol-400 and 350 g of Potassium hydroxide are added, under nitrogen atmosphere. Reaction mixture is then heated under nitrogen, by raising the temperature to about 195-200° C. over a period of about 3-4 h. The same temperature is then, continuously maintained for a period of 24 h. The temperature of the reaction mixture is lowered to a temperature of about 50° C. and diluted with water and extracted with 1 lt of toluene. Toluene is concentrated in order to obtain unreacted 1-[2-(Dimethyl amino-1-(4-methoxyphenyl) ethyl cyclohexanol of about 95 g to about 100 g. Water layer is then acidified to pH 4 to get 1-[2-(Dimethylamino)-1-(4-hydroxyphenypethyl]-cyclohexanol. On drying the mixture at a temperature ranging from about 75° C. to about 80° C. for 8 hours, 1-[2-(Dimethylamino)-1-(4-hydroxyphenypethyl]-cyclohexanol, is obtained (125-130 g) with a purity of 99.25% measured by HPLC). Yield percentage based on recovery of unreacted 1-[2-(Dimethyl amino-1-(4-methoxyphenyl) ethyl cyclohexanol is 98%.

Example 2

To a clean flask, 250 g of 1-[2-(Dimethyl amino-1-(4-methoxyphenyl) ethyl cyclohexanol, 1.5 lt of ethylene glycol, 100 g of polyethylene glycol-400 and 400 g of potassium hydroxide are added, all at once, under nitrogen atmosphere. Reaction mixture is then heated under nitrogen.

Initially, the temperature is raised to about 195-200° C. over a period of 3-4 hours. The same temperature is then, continuously maintained for a period of 48 hours. The temperature of the reaction mixture is lowered to a temperature of about 50° C. and diluted with water and extracted with 1 liter of toluene. Toluene is concentrated in order to obtain unreacted 1-[2-(Dimethyl amino-1-(4-methoxyphenyl) ethyl cyclohexanol of about 45 g. Water layer is then acidified to pH 4 to get 1-[2-(Dimethylamino)-1-(4-hydroxyphenypethyl]-cyclohexanol. On drying the mixture at a temperature ranging from about 75° C. to about 80° C. for 8h, 1-[2-(Dimethylamino)-1-(4-hydroxyphenypethyl]-cyclohexanol the quantity ranging from about 180 g to about 195 g is obtained with a purity of more than 99% measured by HPLC. Yield percentage based on recovery of unreacted 1-[2-(Dimethyl amino-1-(4-methoxyphenyl) ethyl cyclohexanol is 97%.

Example 3

To a clean flask, 250 g of 1-[2-(Dimethyl amino-1-(4-methoxyphenyl) ethyl cyclohexanol 1.25 Lt liter of ethylene glycol, 100 g of polyethylene glycol-400 and 350 g of potassium hydroxide are added, all at once, under nitrogen atmosphere. Reaction mixture is then heated under nitrogen, and the temperature is raised to about 195-200° C., for a period of 3-4 hours. The same temperature is then, continuously maintained for a period of 36 hours. The temperature of the reaction mixture is lowered to a temperature of about 50° C. and diluted with water and extracted with 1 liter of toluene. Toluene is concentrated in order to obtain unreacted 1-[2-(Dimethyl amino-1-(4-methoxyphenyl) ethyl cyclohexanol of about 55 g. Water layer is then acidified to pH 4 to obtain 1-[2-(Dimethylamino)-1-(4-hydroxyphenyl)ethyl]-cyclohexanol. On drying the mixture at a temperature ranging from about 75° C. to about 80° C. degree for 8 h. 1-[2-(Dimethylamino)-1-(4-hydroxyphenypethyl]-cyclohexanol the quantity ranging from about 175 g to about 200 g is obtained with a purity of more than 99% by HPLC. Yield percentage is based on recovery of unreacted 1-[2-(Dimethyl amino-1-(4-methoxyphenyl) ethyl cyclohexanol is 97%.

Example 4

To a clean flask, 250 g of 1-[2-(Dimethyl amino-1-(4-methoxyphenyl) ethyl cyclohexanol, 1 lt of ethylene glycol, 100 g of polyethylene glycol-400 and 605 g of Potassium tert-butoxide are added over a period of 1 h, under nitrogen atmosphere. Reaction mixture is then heated under nitrogen, by raising the temperature to about 195-200° C. over a period of about 3-4 h. The same temperature is then, continuously maintained for a period of 24 h. The temperature of the reaction mixture is lowered to a temperature of about 50° C. and diluted with water and extracted with 1 lt of Toluene. Toluene is concentrated in order to obtain unreacted 1-[2-(Dimethyl amino-1-(4-methoxyphenyl) ethyl cyclohexanol of about 85 g to about 95 g. Water layer is then acidified to pH 4 to get 1-[2-(Dimethylamino)-1-(4-hydroxyphenypethyl]-cyclohexanol. On drying the mixture at a temperature ranging from about 75° C. to about 80° C. for 8 hours, 1-[2-(Dimethylamino)-1-(4-hydroxyphenyl)ethyl]-cyclohexanol, is obtained (115-120 g) with a purity of >99.00% measured by HPLC). Yield percentage based on recovery of unreacted 1-[2-(Dimethyl amino-1-(4-methoxyphenyl) ethyl cyclohexanol is 96%.

The 1-[2-(Dimethylamino)-1-(4-hydroxyphenyl)ethyl]-cyclohexanol thus obtained can be converted to its salt form. The salt is selected from a group comprising succinate, fumarate, oxalate and the like, preferably succinate salt.

The process of synthesis of succinate salt of 1-[2-(Dimethylamino)-1-(4-hydroxyphenyl)ethyl]-cyclohexanol is as follows:

Example 5

To a clean flask, 250 g of 1-[2-(Dimethyl amino-1-(4-methoxyphenyl) ethyl cyclohexanol, 1 lt of ethylene glycol, 100 g of polyethylene glycol-400 and 350 g of potassium hydroxide are added, all at once, under nitrogen atmosphere, Reaction mixture is then heated under nitrogen. Initially the temperature is raised to about 195-200° C. for a period of 3-4 hours. The same temperature is then, continuously maintained for a period of 24 h. The temperature of the reaction mixture is lowered to a temperature of about 50° C. and diluted with water and extracted with 1 lt of toluene. Toluene is concentrated in order to obtain unreacted 1-[2-(Dimethyl amino-1-(4-methoxyphenyl) ethyl cyclohexanol of about 95 g to about 100 g. Water layer is then acidified to pH 4 to get 1-[2-(Dimethylamino)-1-(4-hydroxyphenyl)ethyl]-cyclohexanol. On drying the mixture at a temperature ranging from about 75° C. to about 80° C. degree for 8 hours, 1-[2-(Dimethylamino)-1-(4-hydroxyphenypethyl]-cyclohexanol, the quantity ranging from about 125 g to about 130 g is obtained. The 1-[2-(Dimethylamino)-1-(4-hydroxyphenyl)ethyl]-cyclohexanol is reacted with 56 g of Succinic acid at a temperature 10-50° C. in aqueous acetone (1:3) to obtain succinate salt of 1-[2-(Dimethylamino)-1-(4-hydroxyphenyl)ethyl]-cyclohexanol (130 g) with individual impurity of less than 0.10% of pharmaceutically acceptable salt.

The present invention thus describes an eco-friendly, economical process for synthesis of 1-[2-(Di methylamino)-1-(4-hydroxyphenyl)ethyl]-cyclohexanol also known as Desvenlafaxine from 1-[2-(Dimethyl amino-1-(4-methoxyphenyl) ethyl cyclohexanol also known as Venlafaxine. The process makes use of commercially available reagents with yield ranging from about 97% to about 98%. Thus synthesised 1-[2-(Dimethylamino)-1-(4-hydroxyphenyl)ethyl]-cyclohexanol has a purity of 99% measured by HPLC. The invention also relates to the synthesis of salts of 1-[2-(Dimethylamino)-1-(4-hydroxyphenyl)ethyl]-cyclohexanol. The high yield process is simple and can be easily scaled up for industrial production.

The aforesaid description is enabled to capture the nature of the invention. It is to be noted however that the aforesaid description and the appended figures illustrate only a typical embodiment of the invention and therefore not to be considered limiting of its scope for the invention may admit other equally effective embodiments.

It is an object of the appended claims to cover all such variations and modifications as can come within the true spirit and scope of the invention.

We claim:

1. A process for preparation of 1-[2-(dimethylamino)-1-(4-hydroxyphenyl)ethyl]-cyclohexanol of Formula (I), comprising steps of:

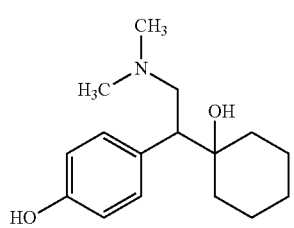

Formula (I)

i) reacting 1-[2-(dimethyl amino-1-(4-methoxyphenyl) ethyl cyclohexanol of Formula (II)

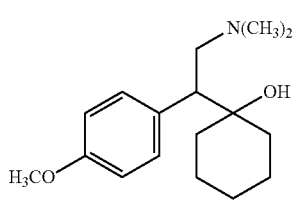

Formula (II)

with at least one potassium salt selected from the group consisting of potassium hydroxide and a potassium alkoxide, in an organic solvent to obtain a mixture;
ii) heating the mixture to a temperature in a range of from about 190° C. to about 220° C.;
iii) diluting the mixture with water to obtain an aqueous phase; and
iv) acidifying the aqueous phase with an acidic reagent, and filtering to obtain the 1-[2-(dimethylamino)-1-(4-hydroxyphenyl)ethyl]-cyclohexanol of Formula (I).

2. The process as claimed in claim 1, wherein the potassium alkoxide is potassium t-butoxide.

3. The process as claimed in claim 1, wherein the organic solvent is at least one selected from the group consisting of monoethylene glycol and an alcohol.

4. The process as claimed in claim 1, wherein acidifying the aqueous phase comprises adjusting the pH between 3 to 5 with the acidic reagent being at least one acid selected from the group consisting of hydrochloric acid, phosphoric acid, and acetic acid.

5. The process as claimed in claim 1, wherein the process provides yield ranging from about 95% to about 99.5%.

6. The process as claimed in claim 1, wherein the 1-[2-(dimethylamino)-1-(4-hydroxyphenyl)ethyl]-cyclohexanol has a purity ranging from about 97.0% to about 99.5% measured by HPLC method.

7. A process for obtaining a salt of 1-[2-(dimethylamino)-1-(4-hydroxyphenyl)ethyl]-cyclohexanol, comprising steps of:
a) reacting 1-[2-(dimethyl amino-1-(4-methoxyphenyl) ethyl cyclohexanol of Formula (II) with at least one potassium salt selected from the group consisting of potassium hydroxide and a potassium alkoxide, in an organic solvent to obtain a mixture;

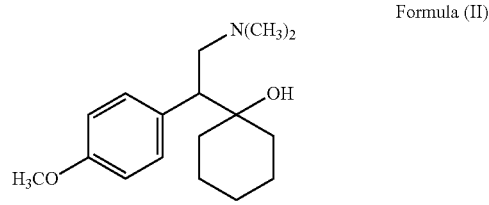 [SMILES: COc1ccc(C(CN(C)C)C2(O)CCCCC2)cc1]

Formula (II)

b) heating the mixture to a temperature in a range of from about 190° C. to about 220° C.;
c) diluting the mixture with water to obtain an aqueous phase;
d) acidifying the aqueous phase with a first acidic reagent and filtering to obtain 1-[2-(dimethylamino)-1-(4-hydroxyphenyl)ethyl]-cyclohexanol of Formula (I); and
e) reacting the 1-[2-(dimethylamino)-1-(4-hydroxyphenyl)ethyl]-cyclohexanol of Formula (I) with a second acidic reagent in an aqueous organic solvent to obtain the salt.

8. The process as claimed in claim 7, wherein the second acidic reagent is at least one selected from the group consisting of succinic acid, fumaric acid, and oxalic acid.

9. The process as claimed in claim 7, wherein the salt of 1-[2-(dimethylamino)-1-(4-hydroxyphenyl)ethyl]-cyclohexanol is of purity ranging from about 98.0 to about 99% measured by HPLC method.

10. The process as claimed in claim 3, wherein the organic solvent is monoethylene glycol.

11. The process as claimed in claim 4, wherein acidifying the aqueous phase comprises adjusting the pH to 4.

12. The process as claimed in claim 8, wherein the second acidic reagent is succinic acid.

13. The process as claimed in claim 1, wherein 1-[2-(dimethyl amino-1-(4-methoxyphenyl) ethyl cyclohexanol of Formula (II) is reacted with potassium hydroxide.

14. The process as claimed in claim 1, wherein 1-[2-(dimethyl amino-1-(4-methoxyphenyl) ethyl cyclohexanol of Formula (II) is reacted with a potassium alkoxide.

15. The process as claimed in claim 7, wherein 1-[2-(dimethyl amino-1-(4-methoxyphenyl) ethyl cyclohexanol of Formula (II) is reacted with potassium hydroxide.

16. The process as claimed in claim 7, wherein 1-[2-(dimethyl amino-1-(4-methoxyphenyl) ethyl cyclohexanol of Formula (II) is reacted with a potassium alkoxide.

\* \* \* \* \*